(12) United States Patent
Fujii et al.

(10) Patent No.: US 6,979,708 B2
(45) Date of Patent: Dec. 27, 2005

(54) HYDROTALCITES, SYNTHESES, AND USES

(75) Inventors: Masaki Fujii, Sewickley, PA (US);
George R. Gallaher, Jr., Oakmont, PA (US); Sehyun Kim, Murrysville, PA (US); Steven J. Monaco, Venetia, PA (US); Edwin B. Townsend, IV, New Kensington, PA (US); Thomas S. Brima, deceased, late of Cincinnati, OH (US); by Gwendolyn Hawk, legal representative, Pittsburgh, PA (US)

(73) Assignee: Sunoco, Inc. (R&M), Philadelphia, PA (US)

( * ) Notice: Subject to any disclaimer, the term of this patent is extended or adjusted under 35 U.S.C. 154(b) by 733 days.

(21) Appl. No.: 09/935,952

(22) Filed: Aug. 23, 2001

(65) Prior Publication Data

US 2003/0078445 A1 Apr. 24, 2003

(51) Int. Cl.$^7$ .............................. C08K 3/10; C08K 5/04
(52) U.S. Cl. ....................... 524/437; 524/394; 524/397; 524/400; 556/27; 556/31
(58) Field of Search ................................. 524/437, 394, 524/397, 400; 556/27, 31

(56) References Cited

U.S. PATENT DOCUMENTS

| | | | |
|---|---|---|---|
| 3,539,306 A | 11/1970 | Kumura et al. ................ 23/315 |
| 4,629,626 A | 12/1986 | Miyata et al. ............... 424/147 |
| 4,729,854 A | * 3/1988 | Miyata et al. ............... 252/609 |
| 4,774,212 A | * 9/1988 | Drezdon ....................... 502/62 |
| 5,064,804 A | 11/1991 | Soo et al. |
| 5,075,355 A | 12/1991 | Hall et al. |
| 5,177,138 A | 1/1993 | Moriyama et al. |
| 5,214,090 A | 5/1993 | Moriyama et al. |
| 5,216,058 A | 6/1993 | Visneski ..................... 524/357 |
| 5,280,065 A | 1/1994 | Moriyama et al. |
| 5,326,891 A | 7/1994 | Breuer et al. |
| 5,348,725 A | 9/1994 | Misra et al. ................. 423/594 |
| 5,399,329 A | * 3/1995 | Schutz et al. ............ 423/415.1 |
| 5,470,910 A | 11/1995 | Spanhel et al. ............. 524/785 |
| 5,507,980 A | 4/1996 | Kelkar et al. |
| 5,518,704 A | 5/1996 | Kelkar et al. |
| 5,578,286 A | 11/1996 | Martin et al. ................ 423/593 |
| 5,595,747 A | 1/1997 | Kuroda et al. ............... 424/405 |
| 5,698,624 A | 12/1997 | Beall et al. .................. 524/445 |
| 5,728,364 A | 3/1998 | Martin et al. ................ 423/593 |
| 5,728,366 A | * 3/1998 | Martin et al. ............. 423/594.1 |
| 5,760,121 A | 6/1998 | Beall et al. .................. 524/450 |
| 5,844,032 A | 12/1998 | Serrano et al. ............. 524/445 |
| 5,849,830 A | 12/1998 | Tsipursky et al. ........... 523/450 |
| 5,877,248 A | 3/1999 | Beall et al. .................. 524/450 |
| 5,910,523 A | 6/1999 | Hudson |
| 5,962,553 A | 10/1999 | Ellsworth .................... 523/216 |
| 5,973,053 A | 10/1999 | Usuki et al. |
| 5,977,218 A | * 11/1999 | Bonora ......................... 524/91 |
| 6,313,208 B1 | * 11/2001 | Nosu et al. .................. 524/437 |

FOREIGN PATENT DOCUMENTS

| | | |
|---|---|---|
| JP | 57200433 | 12/1982 |
| JP | 58013643 | 1/1983 |
| JP | 59011308 | 1/1984 |
| JP | 10036589 | 2/1998 |

OTHER PUBLICATIONS

Carlino S. "The intercalation of carboxylic acides into layered double hydroxides: a critical evaluation and review of the different methods," Solid State Ionics, North Holland Publishing Company, Amsterdam, NL, vol. 98, No. 1–2, Jun. 1, 1997, pp. 73–84.

Borja, M. et al. "Fatty Acids in Layered Metal Hydroxides: Membrane–Like Structures and Dynamics," Journal of Physical Chemistry, American Chemical Society, U.S., vol. 96, No. 13, 1992, pp. 5434–5444.

* cited by examiner

Primary Examiner—Tae H. Yoon
(74) Attorney, Agent, or Firm—Buchanan Ingersoll PC; Robert A. Koons, Jr., Esq.; Gary D. Mangels

(57) ABSTRACT

Synthetic hydrotalcites of the general formula $$[M^{2+}_{1-x}M^{3+}_{x}(OH)_2]^{x+}[A^{n-}_{x/n} \cdot mH_2O]^{x-}$$

where $M^{2+}$ is a divalent cation, $M^{3+}$ is a trivalent cation and $A^{n-}$ is an organic anion selected from straight chain carboxylates of $C_{16}$–$C_{18}$ acids, carboxylates of aromatic acids, carboxylates of acrylic acid, unsaturated carboxylates of methacrylic acid and unsaturated carboxylates of vinylacetic acid are disclosed, along with methods of synthesis and uses.

39 Claims, 10 Drawing Sheets

Figure 8
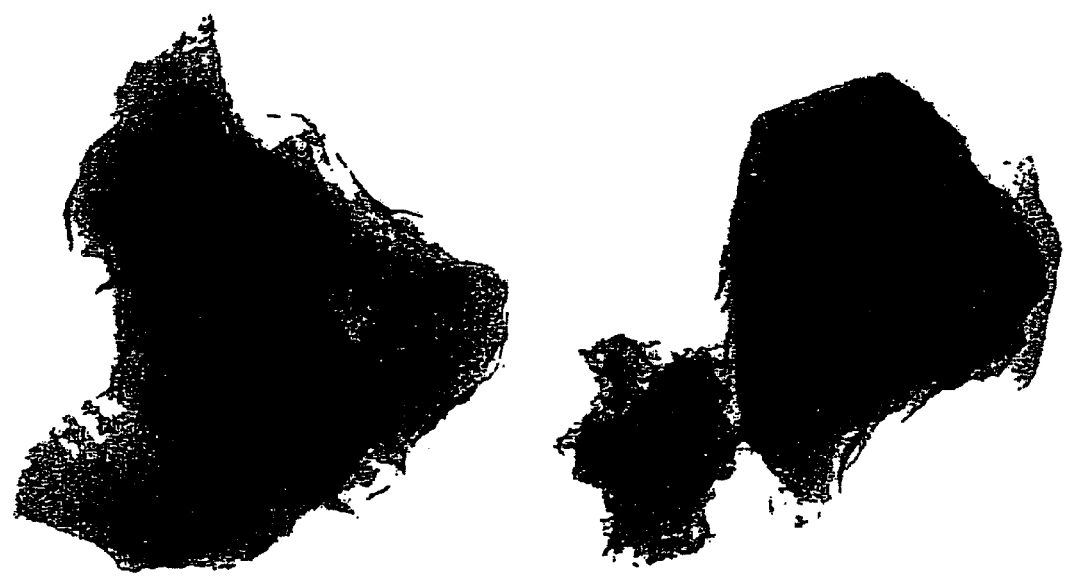

HYDROTALCITES, SYNTHESES, AND USES

FIELD OF THE INVENTION

This invention relates in general to catalysts and, more specifically, to novel synthetic hydrotalcites, their syntheses and uses. The synthetic hydrotalcites of the present invention are made from organic anions longer than $C_4$, and also from organic anions with functional groups including saturated carboxylates of $C_6$, $C_8$, $C_{10}$, and $C_{18}$, straight chain acids; aromatics such as benzoates, chlorobenzoates, naphthoates, and p-hydroxybenzoates; carboxylates of acrylic, methacrylic and vinylacetic acids; and mixtures of these organic anions.

BACKGROUND OF THE INVENTION

Hydrotalcites are derivatives of brucite, a naturally-occurring, layered, magnesium hydroxide mineral. Synthetic hydrotalcites can be made by substituting a trivalent metal cation, such as aluminum, for some of the magnesium cations normally present in a layer. The magnesium cations can also be substituted by other divalent cations. This substitution will result in a net positive charge residing on the layer, which requires an intercalating anion to achieve a net neutral charge for the molecule. The following general formula has been derived for synthetic hydrotalcites.

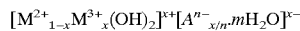

$$[M^{2+}_{1-x}M^{3+}_x(OH)_2]^{x+}[A^{n-}_{x/n}\cdot mH_2O]^{x-}$$

wherein $M^{2+}$ is magnesium and/or other divalent cation, $M^{3+}$ is aluminum and/or other trivalent cation and $A^{n-}$ is an anion. In addition to the anion, it will be noted that water is also a part of the lattice structure.

A group of hydrotalcites with a unique sheet-like morphology is described in U.S. Pat. No. 5,399,329, issued to Schutz, et. al., and assigned to the assignee of the present invention. The entire contents of the Schutz '329 patent are incorporated herein by reference. The hydrotalcites of the Schutz '329 patent are comprised of anions derived from $C_1$ to $C_4$ saturated carboxylic acids. The general synthetic method of the Schutz '329 patent involves the reaction of an alumina source with a carboxylic acid in water followed by the reaction of the resulting mixture with a magnesium source. The approximate molar ratio of the reagents is as follows: 2 Mg:1 Al:1 anion; with the anion being the carboxylate of the acid used.

Although a hexagonal morphology is normally observed for non-carboxylate anion hydrotalcites, the carboxylate anion hydrotalcites of the Schutz '329 patent exhibit a unique morphology, termed therein "sheet-like". The distance between the hydrotalcite layers, as measured by d spacing, depends on the size of the intercalating anion. For example, carboxylate hydrotalcites from the following anions produced by the method of the Schutz '329 patent have a d spacing of: formate 7.64 Å, acetate 12.3 Å, propionate 13.02 Å, and isobutyrate 15.15 Å.

In the Schutz '329 patent, sheet-like hydrotalcites are prepared in aqueous medium by reacting alumina with a carboxylic acid at about 60° C. for 30 minutes followed by the addition of magnesium oxide at a temperature of 95° C. for about 6 hours. The desired gel hydrotalcite is obtained upon drying the reaction product. Although the method of the Schutz '329 patent works rather well for most water-soluble carboxylic acids such as $C_1$ to $C_4$ carboxylic acids, it does not work well for those acids, which are water-insoluble. In fact, butyric acid, which is a $C_4$ acid, has only limited success in the method of the Schutz '329 patent.

Hydrotalcites have many uses, including such applications as catalysts or catalyst precursors, ion exchangers, ion absorbers, ion-scavengers, and medical uses as antacids. Hydrotalcites are also used as nanocomposites in polymers to provide various property enhancements.

In Japanese Patent Application 96-189168, assigned to Mitsui Petrochem Ind. Ltd., naturally-occurring hydrotalcites containing a carbonate anion are used in polypropylene synthesis, along with other additives, and are said to give good melt flow index, flexural modulus and Izod impact strength.

In EP 0,910,131, assigned to AtoChem, Fr., naturally-occurring hydrotalcites containing a carbonate anion are used in an ethylene-vinylacetate copolymer and are said to produce a film with good adhesion and barrier properties.

In Japanese Patent Application 86-296799, assigned to Du-Pont Mitsui Polychemicals Co., Ltd., naturally-occurring hydrotalcites containing a carbonate anion are used in linear, low density polyethylene and are said to produce a film which has thermal insulating properties and good tensile strength.

Most nanocomposite polymer applications use pillared clays and/or naturally-occurring hydrotalcites. Compounded compositions of nylon-6 and 5% clay nanocomposites have been shown to exhibit a 40% higher tensile strength, 68% greater tensile modulus, 60% higher flexural strength and a 126% flexural modulus (See, Int'l. SAMLE Symp. Exhib. 1998, 43:1053–1066). Nanocomposites are believed to disperse in the polymer in one of the following two ways:

1) in a disorderly fashion, such as by intercalation; or
2) by exfoliation, in which the nanolayers are regularly spaced in the polymer. Exfoliation is believed to lead to improved polymer properties.

Therefore, a need exists in the art for new synthetic hydrotalcites made from organic anions longer than $C_4$ and also those with functional groups including saturated carboxylates of $C_6$, $C_8$, $C_{10}$ and $C_{18}$ straight chain acids; aromatics such as benzoates, chlorobenzoates, naphthoates, and p-hydroxybenzoates; carboxylates of acrylic, methacrylic and vinylacetic acids; and mixtures of these organic anions. Such new synthetic hydrotalcites can find among their uses, that as nanocomposites in polymer applications, because these synthetic hydrotalcites are customizable according to the properties desired in the polymers made therefrom.

SUMMARY OF THE INVENTION

The present invention provides a synthetic hydrotalcite of the general formula,

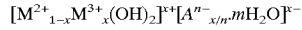

$$[M^{2+}_{1-x}M^{3+}_x(OH)_2]^{x+}[A^{n-}_{x/n}\cdot mH_2O]^{x-}$$

wherein $M^{2+}$ is a divalent cation, $M^{3+}$ is a trivalent cation and $A^{n-}$ is an organic anion selected from straight chain carboxylates of $C_5$–$C_{18}$ acids, carboxylates of aromatic acids, carboxylates of acrylic acid, unsaturated carboxylates of methacrylic acid and unsaturated carboxylates of vinylacetic acid.

The present invention also provides a synthetic hydrotalcite of the general formula

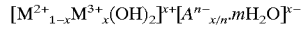

$$[M^{2+}_{1-x}M^{3+}_x(OH)_2]^{x+}[A^{n-}_{x/n}\cdot mH_2O]^{x-}$$

wherein $M^{2+}$ is a divalent cation, $M^{3+}$ is a trivalent cation and $A^{n-}$ is an anion comprising a mixture of at least two members of the group consisting of straight chain saturated carboxylates of $C_2$–$C_4$ acids, carboxylates of aromatic acids, carboxylates of acrylic acid, unsaturated carboxylates of methacrylic acid and unsaturated carboxylates of vinylacetic acid.

The present invention further provides for a method of making a synthetic hydrotalcite of the general formula, $$[M^{2+}_{1-x}M^{3+}_x(OH)_2]^{x+}[A^{n-}_{x/n}\cdot mH_2O]^{x-}$$

wherein $M^{2-}$ is a divalent cation source, $M^{3+}$ is a, trivalent cation source and $A^{n-}$ is an organic anion source selected from straight chain carboxylates of $C_5$–$C_{18}$ acids, carboxylates of aromatic acids, carboxylates of acrylic acid, unsaturated carboxylates of methacrylic acid and unsaturated carboxylates of vinylacetic acid, the method comprising: reacting the trivalent cation source with the organic anion source to produce an intermediate and reacting the intermediate with the divalent cation source to produce the synthetic hydrotalcite.

The present invention still further provides for a synthetic hydrotalcite-polyolefin blend comprising a polyolefin and a synthetic hydrotalcite of the general formula, $$[M^{2+}_{1-x}M^{3+}_x(OH)_2]^{x+}[A^{n-}_{x/n}\cdot mH_2O]^{x-}$$

wherein $M^{2+}$ is a divalent cation, $M^{3+}$ is a trivalent cation and $A^{n-}$ is an organic anion selected from straight chain carboxylates of $C_5$–$C_{18}$ acids, carboxylates of aromatic acids, carboxylates of acrylic acid, unsaturated carboxylates of methacrylic acid and unsaturated carboxylates of vinylacetic acid.

The present invention yet further provides a method for making a synthetic hydrotalcite-polyolefin blend comprising: mixing a polyolefin emulsion with a synthetic hydrotalcite of the general formula, $$[M^{2+}_{1-x}M^{3+}_x(OH)_2]^{x+}[A^{n-}_{x/n}\cdot mH_2O]^{x-}$$

wherein $M^{2+}$ is a divalent cation source, $M^{3+}$ is a trivalent cation source and $A^{n-}$ is an organic anion source selected from straight chain carboxylates of $C_5$–$C_{18}$ acids, carboxylates of aromatic acids, carboxylates of acrylic acid, unsaturated carboxylates of methacrylic acid and unsaturated carboxylates of vinylacetic acid, to obtain the blend.

BRIEF DESCRIPTION OF THE FIGURES

The present invention will be described for the purposes of illustration, but not limitation in conjunction with the following figures, wherein:

FIG. 8 is a micrograph of a blend of about 81% hydrotalcite with polypropylene demonstrating the preferred "cabbage morphology";

DETAILED DESCRIPTION OF THE INVENTION

Figure 1:
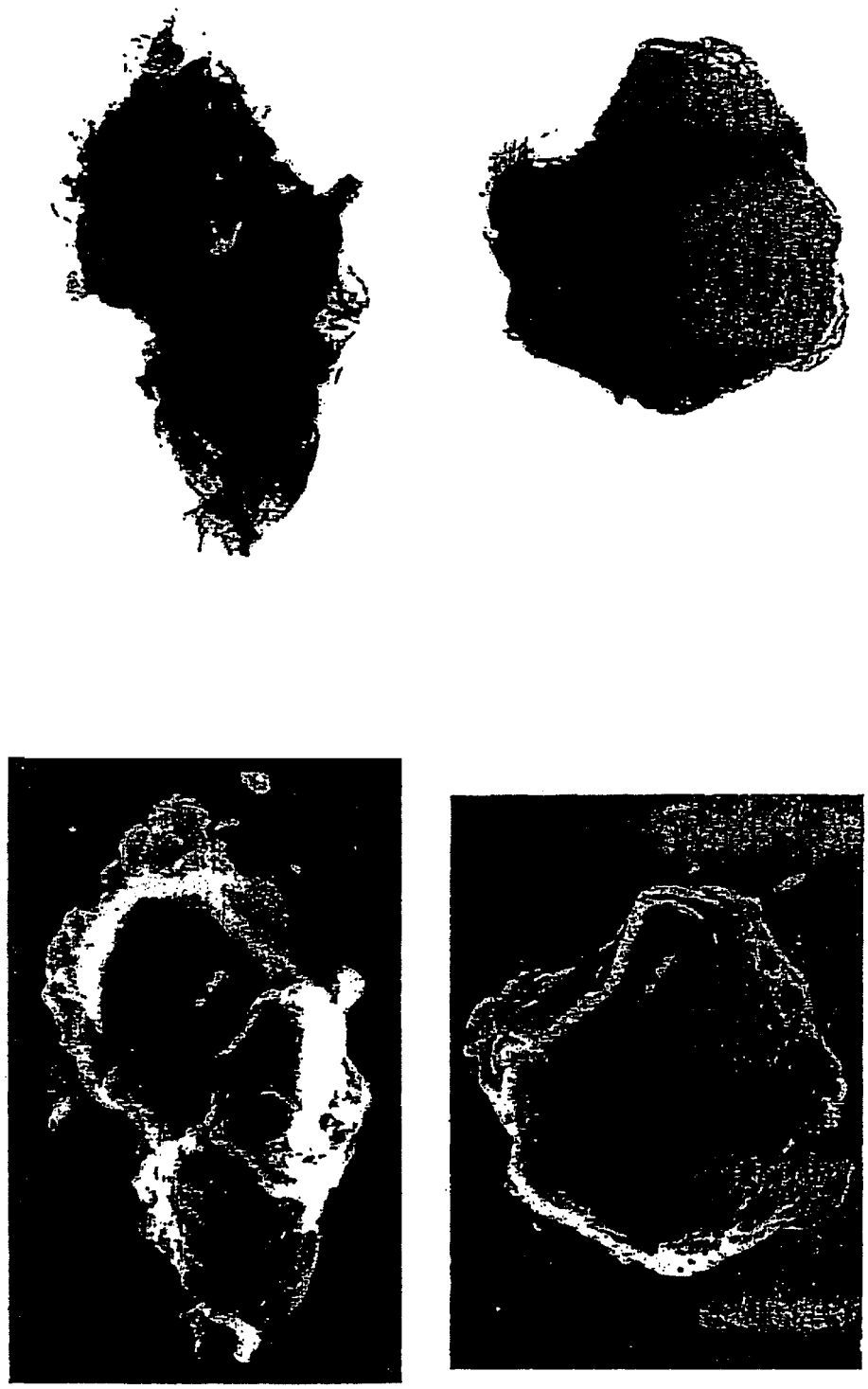
FIG. 1 is a micrograph of a synthetic hydrotalcite made in Example 1.

The three general steps of synthesizing hydrotalcites of the present invention are given below.

Step I: Trivalent Cation Source+Organic Anion→Intermediate

60°–75° C., 4–8 hours

Step II: Intermediate (in Water)+Divalent Cation Source→Synthetic Hydrotalcite Gel 90°–95° C., 4–8 hours Step III: Dry (Evaporate/dry under vacuum, filter/dry under vacuum or spray-dry)

Success in preparing the synthetic hydrotalcites of the present invention depends greatly on the complete reaction in Step I, i.e., the trivalent cation reacting with the specific carboxylic acid. The preparation of hydrotalcites from longer chain than $C_4$ carboxylic acids and water-insoluble aromatic acids is accomplished by driving the reaction of Step I closer to completion preferably by utilizing one or more of the following approaches:

1) the reaction time for Step I can be increased from 30 minutes, as in the Schutz '329 patent, to from 4 to 8 hours;

2) inert organic solvents can be used as a reaction media for water insoluble-organic carboxylic acids with the trivalent cation source; and 3) Step I can be carried out in a melt of the organic anion.

In the examples described herein, the following materials were used: Trivalent cation source, unless otherwise specified was CATAPAL® alumina which is aluminum oxide monohydroxide from Vista Chemical Corporation; divalent cation source: Martin Magnesia Specialties Inc. MAGCBEM® 200D (a high purity, highly reactive magnesium oxide powder); acids were from Aldrich Chemical Company; and maleated nonionic polypropylene emulsion was from CHEMCOR containing 39–41% non-volatiles, Trade Name: POLY EMULSION 43N40® (used in the hydrotalcite-polypropylene blend preparation).

The scanning electron microscopy (SEM) analyses of the synthetic hydrotalcite samples of the present invention were carried out by R J Lee Group, Inc of Monroeville, Pa., USA. The analyses required collecting photomicrographs utilizing both secondary electron imaging (SEI) and transmission electron imaging (TED of typical particles in the samples. Three different typical particles from each sample were micrographed at magnifications ranging from 5,000× to 50,000× depending on the size of the particles.

Spray-Drying Method

Spray-drying of the synthetic hydrotalcites of the present invention can preferably be performed by using a Niro-2 fluid nozzle spray-dryer with the following settings: heat at 5.5, air pressure to the nozzle at 1 bar and the inlet temperature maintained at desired set range of 200–230° C. by varying the liquid feed rate (4–5 liters/hr). Water can preferably be fed to the spray-dryer after the temperature is stabilized to estimate the required feed rate and to remove any material remaining from a previous use.

Synthetic Hydrotalcite Preparation

As was mentioned previously, preparation of the synthetic hydrotalcites of the present invention is carried out in three steps. In Step I, the organic anion source is reacted with a trivalent cation source, preferably $Al^{3+}$, but as demonstrated in U.S. Pat. No. 5,518,704 incorporated herein in its entirety by reference, mixtures of $Al^{3+}$ and up to 50% of at least one of the other trivalent cations, $Cr^{3+}$ and $Fe^{3+}$, may also be used in synthetic hydrotalcite preparation. Step II is the reaction of the mixture from Step I with a divalent cation source, preferably $Mg^{2+}$, but as demonstrated in U.S. Pat. No. 5,518,704 incorporated herein in its entirety by reference, mixtures of $Mg^{2+}$ and at least one of the other divalent cations, $Ni^{2+}$, $Co^{2+}$, $Zn^{2+}$, $Cu^{2+}$, and $Mn^{2+}$, may also be used in synthetic hydrotalcite preparation. Step III is drying the resultant synthetic hydrotalcite. The Inventors have discovered that Step I of the preparation may be carried out in water, in an organic solvent, or in an acid melt, depending on the water solubility of the organic anion. Step II preferably is carried out in water.

By way of illustration and not limitation, preparations of a stearic acid synthetic hydrotalcite by methods utilizing each of the three approaches to improve Step I will now be described.

EXAMPLE 1

Step I Carried Out in Water Medium

CATAPAL® alumina (0.26 moles) was suspended in 500 ml deionized water in a 4-liter beaker and stearic acid (0.23 moles) was added to the stirred suspension. The beaker was fitted with a crystallizing dish filled with ice water to condense volatiles in the beaker as it was heated to 75°–85° C. and the temperature was maintained for 4 to 8 hours. At the end of this period, magnesium oxide (0.44 moles) was added, followed by 1.5 liters of deionized water. The mixture was heated to 90°–95° C. and the temperature was maintained for 4 to 8 hours. The mixture was cooled to room temperature overnight with stirring. The resulting material can preferably be dried in one of two ways:

a) in an air oven at 130° C. until a semi-dry solid is obtained, which is further dried in a vacuum oven at 80° C. overnight; or b) by spray-drying at approximately 200° C. inlet temperature and about 100° C. outlet temperature.

The powder obtained after drying the material is the intended synthetic hydrotalcite.

In water medium, a smaller than usual amount of water preferably is used, otherwise the acid may float above the alumina suspension in the water and slow the reaction rate. The product of this reaction was a greasy oil that was denser than the medium and settled to the bottom of the reaction vessel. In such a medium, some of the alumina and the free acid may be trapped and either react very slowly, or not at all, because mixing of the reagents becomes highly limited. The synthetic hydrotalcite made by this approach was not very homogenous as can be seen by reference to FIG. 1, which is a scanning electron micrograph of the sample.

EXAMPLE 2

Step I Carried Out in Organic Solvent(s)

Figure 2:
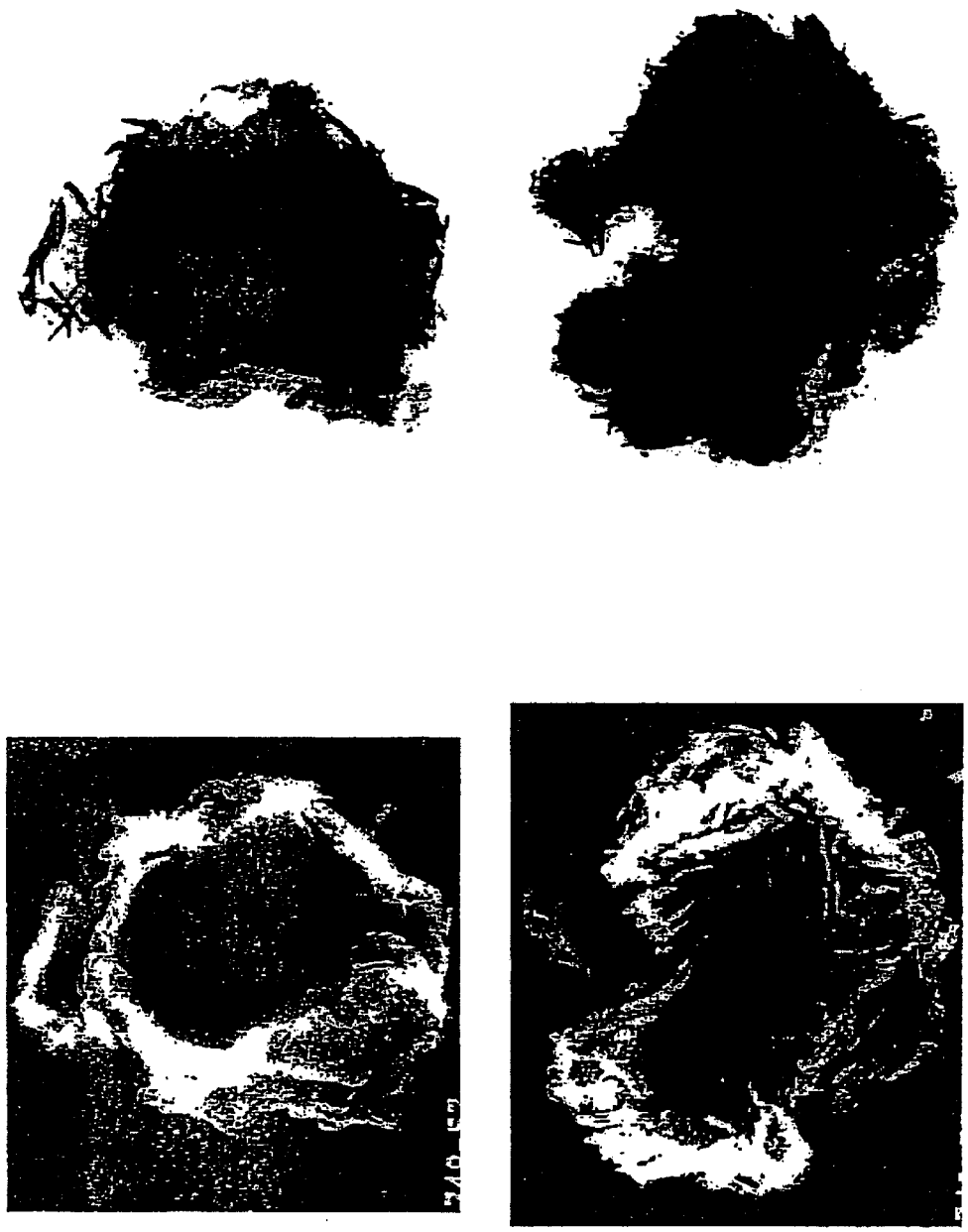
FIG. 2 is a micrograph of a synthetic hydrotalcite made in Example 2.

The reaction of the trivalent cation source and carboxylic acids that are water immiscible, such as stearic acid, can preferably be carried out in an organic solvent, such as refluxing hexane. CATAPAL® alumina (0.26 moles) was suspended in 200 ml hexane in a 4-liter beaker and the acid (0.23 moles) was added to the stirred suspension. The beaker was fitted with a crystallizing dish filled with ice water to condense volatiles in the beaker as it was heated to about 65° C. and the temperature was maintained for 4 to 8 hours. The solvent may preferably be removed by evaporation or filtration. Water was added to the resulting residue. Magnesium oxide (0.44 moles) was then added with vigorous stirring. The mixture was heated to about 90°–95° C. and the temperature was maintained for 4 to 8 hours. Product isolation, i.e., drying, was carried out as described in Example 1 above. Using this approach, a homogenous synthetic hydrotalcite was obtained with a larger d spacing value and with a seemingly smaller particle size as indicated by SEM, which can be seen by comparison of FIG. 1 to FIG. 2.

When Step I is carried out in an organic solvent, a faster, exothermic reaction occurs which results in an intermediate which is soluble in the medium. A disadvantage of this approach, however, is that the solvent preferably be removed before the reaction of the intermediate with the divalent cation source, because Step H is preferably carried out in water.

EXAMPLE 3

Step I Carried Out in an Acid Melt

A beaker containing the required amount of solid stearic acid was heated on an oil bath until the acid melted. The desired stoichiometric amount of alumina was added in small portions to the melt with stirring. The temperature was maintained for about two or more hours. Water was added to the product, and the mixture was stirred to an even consistency. Magnesium oxide was added, followed by 1.5 liters of deionized water. The mixture was heated to 90°–95° C. and the temperature was maintained for 4 to 8 hours. The mixture was allowed to cool to room temperature overnight with stirring. Product isolation was carried out as in Example 1 above.

A difficulty encountered with this approach was similar to that observed in Example 1, i.e., the product was greasy. However, an advantage of using the acid melt approach is that the reaction rate in an acid melt is much faster than that observed in water. With adequate mixing in the acid melt, a more complete reaction than that in water is expected. This may provide an economical approach in preparing synthetic hydrotalcites of solid fatty acids, which have moderate melting temperatures. The acid melt approach is faster than the water approach due to a faster reaction rate and it is faster than the organic solvent approach because there is no need to remove an organic solvent before proceeding to Step II. Table I summarizes the d spacing, the interlayer distance and the particle size of synthetic hydrotalcites made by each approach.

TABLE I

COMPARISON OF APPROACHES TO
SYNETHESIZING STEARIC ACID HYDROTALCITE

| Example No. | Organic Anion Source | Step 1 Medium | d spacing Å | Interlayer Distance Å | Particle Size Microns |
|---|---|---|---|---|---|
| 1 | Stearic acid | Water | 19.4 | 14.6 | 11 × 6 |
| 2 | Stearic acid | Organic Solvent | 26.4 | 21.6 | 3 × 3 |
| 3 | Stearic acid | Acid melt | 24.4 | 19.6 | 5 × 3 |

EXAMPLES 4–20

Synthetic hydrotalcites from the following organic anion sources were prepared by the methods of the present invention and some properties of these synthetic hydrotalcites are summarized in Table II: stearic acid; glycolic acid; acetic acid; acrylic acid; γ-butyrolactone; ethanesulfonic acid; lactic acid; hexanoic acid; octanoic acid; decanoic acid; benzoic acid; chlorobenzoic acid; cinnamic acid; naphthoic acid; methacrylic acid; acrylic acid, vinylacetic acid; a mixture of acrylic, acetic, and stearic acids; and a mixture of acetic, hexanoic, and stearic acids.

Figure 3:
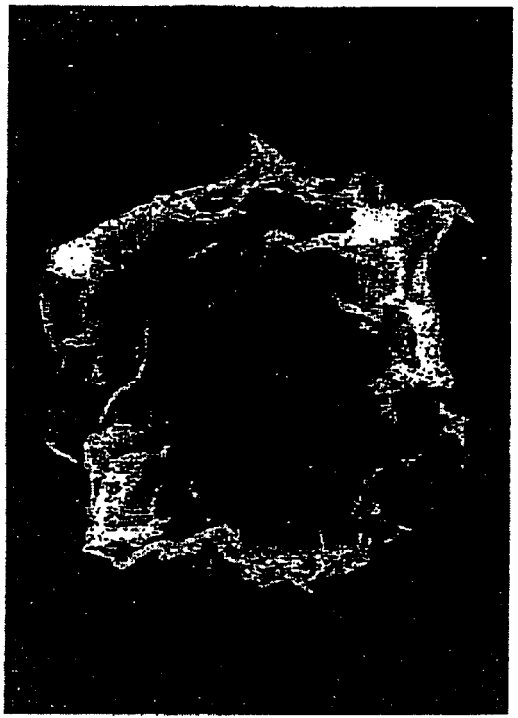
FIG. 3 is a micrograph of a benzoic acid-derived synthetic hydrotalcite.
Figure 3:
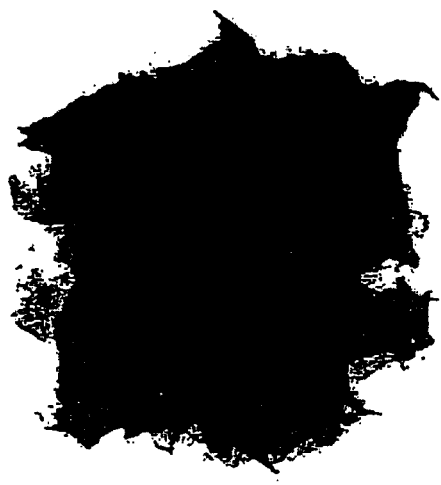
Figure 3:
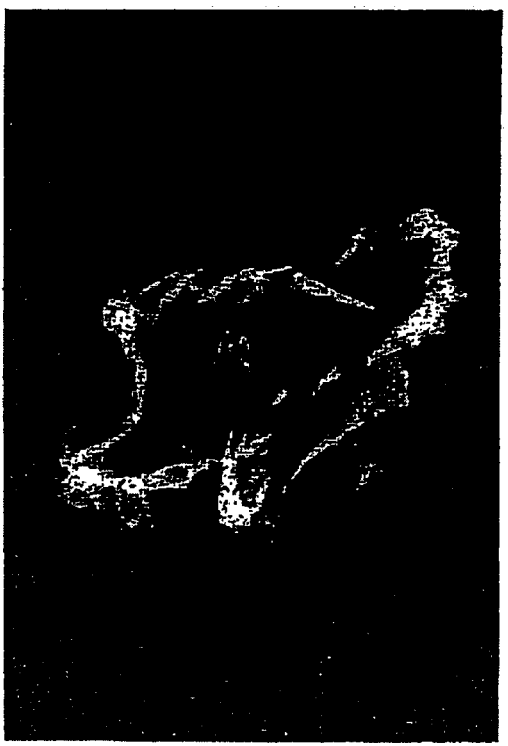
Figure 3:
Figure 4:
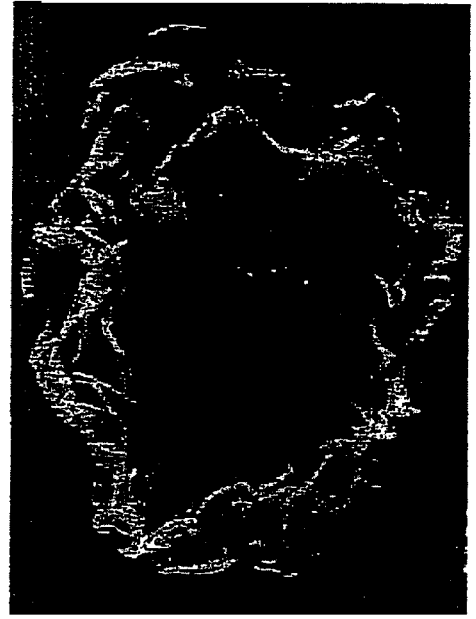
FIG. 4 is a micrograph of a methacrylic acid-derived synthetic hydrotalcite.
Figure 4:
Figure 4:
Figure 4:
Figure 5:
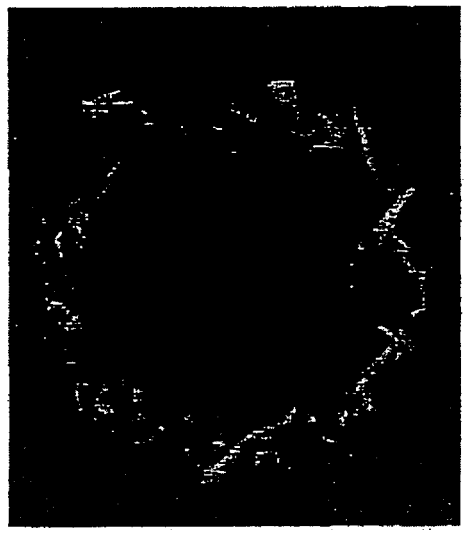
FIG. 5 is a micrograph of an acrylic acid-derived synthetic hydrotalcite.
Figure 5:
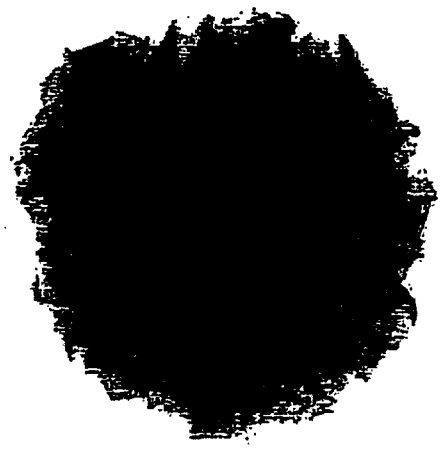
Figure 5:
Figure 5:

With longer reaction times for Step I, synthetic hydrotalcites of the following organic anion sources can be prepared in water: ethanesulfonic acid, lactic acid, benzoic acid, methacrylic acid, acrylic acid, and vinylacetic, acid. FIGS. 3–5 are scanning electron micrographs of three representative members of this group: benzoic acid, methacrylic acid, and acrylic acid, respectively.

All of the synthetic hydrotalcites described herein were analyzed by x-ray diffraction analysis (XRD) for the x-ray peak position, intensity and d spacing. The d-spacing is indicative of the distance between the layers in the hydrotalcite, because it is dependent upon the size and the shape of the anion in the hydrotalcite and is given for each of the synthetic hydrotalcites in Table II. The assumption that synthetic hydrotalcites with larger d spacing would mix with or exfoliate in polymers led to the synthesis of those hydrotalcites with larger anions or anions with longer carbon chains.

Figure 6:
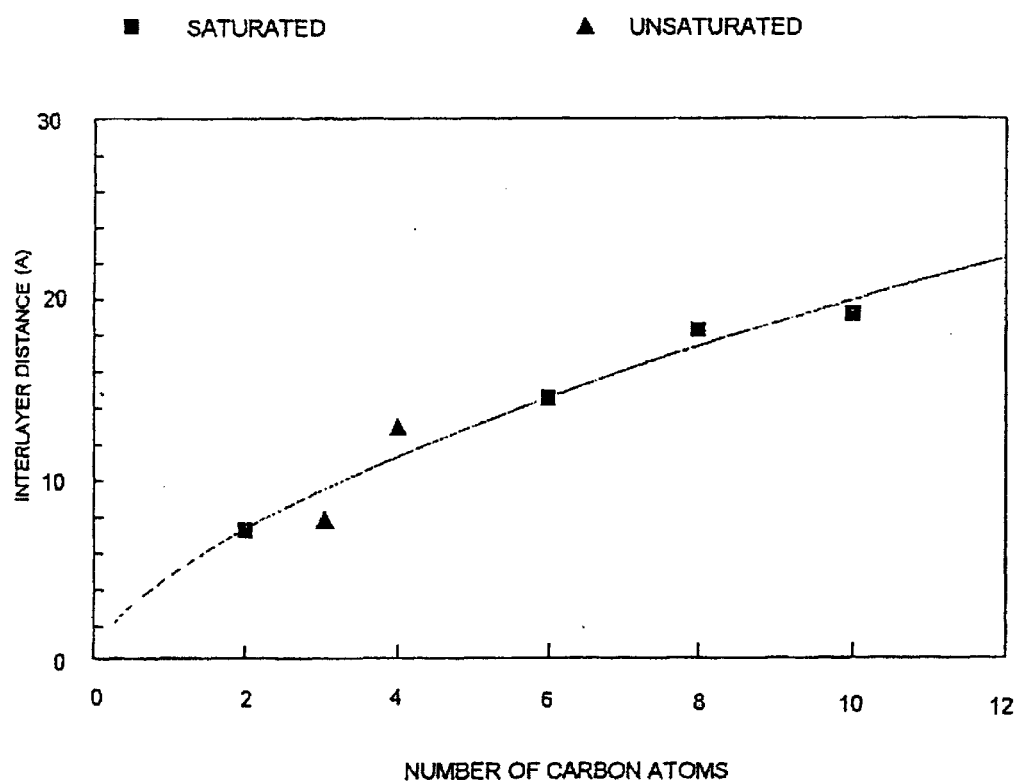
FIG. 6 illustrates the predicted relationship between interlayer distance and the number of carbon atoms in an anion.

FIG. 6 shows that as the number of carbon atoms in the anion increases, so does the hydrotalcite interlayer distance. This interlayer distance equals the d spacing minus the brucite layer thickness of 4.77 Å. In fact, there is a good correlation between the number of carbon atoms (at least up to $C_{10}$) in the organic anion and the interlayer distance. The highest interlayer distance obtained for the synthetic hydrotalcite made from stearic acid is 21.6 Å, which does not fit well in the prediction made from looking at FIG. 6. A predicted fit would be 26.0 Å, suggesting perhaps that beyond a certain number of carbon atoms there is enough flexibility in the carbon chain backbone to cause a deviation from the prediction.

Synthetic hydrotalcites which had a d spacing equal to or higher than 12 Å, the d spacing for acetic acid hydrotalcite, were subjected to SEM analysis to obtain the particle size, overall dimensions of the particles and the morphology for the synthetic hydrotalcite. As in the Schutz '329 patent, the preferred morphology for hydrotalcites of the present invention is sheet-like, herein termed "cabbage". Excellent examples of this morphology were obtained for the synthetic hydrotalcites prepared from the following anions: acetic, ethanesulfonic, octanoic, benzoic, chlorobenzoic, methacrylic, acrylic, and vinylacetic acids.

Figure 7:
FIG. 7 is a micrograph of a mixture of acetic, hexanoic, and stearic acids-derived synthetic hydrotalcite demonstrating a "semi cabbage" morphology.
Figure 7:
Figure 7:
Figure 7:

Other synthetic hydrotalcites which have a morphology herein described as "semi-cabbage" were those derived from the following anion sources: stearic acid, decanoic acid, naphthoic acid, mixed stearic, acrylic and acetic acids; mixed acetic, hexanoic and stearic acids, (See FIG. 7). "Semi-cabbage" as used herein means that only one or two of the three representative particles selected for micrography exhibited the cabbage morphology.

Without being limited to any specific theory, the Inventors believe that a possible explanation for this semi-cabbage morphology may be that the size and/or shape of the organic anion prevents it from conforming to the true cabbage formation within the crystal structure. Alternatively, the long carbon chain anion and the interlayer water molecules in the synthetic hydrotalcite structure may repel each other, thereby leading to a distortion in the crystal structure. It is also possible that an incomplete reaction with the trivalent cation in Step I of the hydrotalcite synthesis may lead to a semi-cabbage morphology.

Preparations carried out in water, which failed to result in synthetic hydrotalcites with the desired morphology, were from the following anion sources: glycolic acid, γ-butyrolactone and lactic acid. One possible explanation for the failure to produce synthetic hydrotalcites with the desired morphology from these water-soluble anion sources may be crosslinking between the layers due to the existence of double anions (carboxylate and hydroxylic) as indicated by solid state NMR.

The average size of the particles was measured in microns using the rulers shown in the SEM micrographs. A smaller particle size is preferred when the intended use for the synthetic hydrotalcite is in a nanocomposite. The particles of the synthetic hydrotalcites of the present invention are generally in the micron range as can be appreciated from a review of the data contained in Table II. The method of drying the synthetic hydrotalcites of the present invention did not seem to have any effect on the particle size.

Comparative Examples 22–24

Synthetic hydrotalcites made from a commercially available hydrotalcite (LaRoche, acetate anion HTC-0498-10), methacrylic, and acrylic acids with flash calcined alumina (FCA, available from LaRoche Industries) as the trivalent cation source gave a morphology that can, at best, be described as semi-cabbage. SEM indicated that more than one aluminum compound exists in FCA or that its reactivity with the acid is lower compared to CATAPAL® alumina. As can be appreciated from reference to Table II, the d spacing for HTC-0498-10 (Comparative Example 22) was 9.7 Å compared to 12.0 Å for a comparable synthetic hydrotalcite prepared in the assignee's laboratory from CATAPAL® alumina and acetic acid (Example 5).

TABLE II

SOME PROPERTIES OF SYNTHETIC HYDROTALCITES

| Example No. | Organic Anion Source | d spacing Å | Interlayer Distance Å | Particle Morphology | Particle Size microns |
|---|---|---|---|---|---|
| 1 | Stearic acid | 19.4 | 14.6 | semi-cabbage | 11 × 6 |
| 2 | Stearic acid[1] | 26.4 | 21.6 | semi-cabbage | 3 × 3 |
| 3 | Stearic acid[2] | 24.4 | 19.6 | Semi-cabbage | 5 × 3 |
| 4 | Glycolic acid | 9.2 | 4.4 | clump | 2 × 1 |
| 5 | Acetic acid | 12.0 | 7.2 | cabbage | 6 × 4 |
| 6 | γ-Butyrolactone | 12.3 | 7.5 | clump | 2 × 2 |
| 7 | Ethanesulfonic acid | 14.8 | 10.0 | cabbage | 6 × 3 |
| 8 | Lactic acid | 15.0 | 10.2 | Semi-cabbage | 3 × 4 |
| 9 | Hexanoic acid | 19.2 | 14.4 | clump | 5 × 3 |
| 10 | Octanoic acid | 22.9 | 18.1 | Semi-cabbage | 5 × 4 |
| 11 | Decanoic acid | 23.9 | 19.1 | Semi-cabbage | 4 × 3 |
| 12 | Benzoic acid | 17.0 | 12.2 | cabbage | 4 × 3 |
| 13 | Chlorobenzoic acid | 16.8 | 12.0 | cabbage | 3 × 4 |
| 14 | Cinnamic acid | 18.4 | 13.6 | clump | 7 × 4 |
| 15 | Naphthoic acid | 19.2 | 14.4 | Semi-cabbage | 6 × 6 |
| 16 | Methacrylic acid | 13.2 | 8.4 | cabbage | 6 × 5 |
| 17 | Acrylic acid | 16.6 | 11.8 | cabbage | 3 × 3 |
| 18 | Vinylacetic acid | 17.7 | 12.9 | cabbage | 6 × 4 |
| 19 | Mixed acids[3] | 15.5 | 10.7 | Semi-cabbage | 3 × 2 |
| 20 | Mixed acids[4] | 16.4 | 11.6 | Semi-cabbage | 6 × 3 |
| 21 | Octanoic acid | 20.3 | 15.5 | cabbage | 5 × 2 |

TABLE II-continued

SOME PROPERTIES OF SYNTHETIC HYDROTALCITES

| Example No. | Organic Anion Source | d spacing Å | Interlayer Distance Å | Particle Morphology | Particle Size microns |
|---|---|---|---|---|---|
| Comp. Ex 22 | HTC-0498-10 | 9.7 | 4.9 | Semi-cabbage | 11 × 5 |
| Comp. Ex 23 | Methacrylic acid[5] | 14.0 | 9.2 | Semi-cabbage | 11 × 8 |
| Comp. Ex 24 | Acrylic acid' | 13.8 | 9.0 | Semi-cabbage | 7 × 5 |

[1]Step I of preparation was carried out in hexane solvent.
[2]Step I of preparation was carried out in stearic acid melt without a solvent.
[3]Mixture molar composition: 3.76 acrylic acid:1.14 acetic acid:0.57 stearic acid.
[4]Mixture molar composition: 1.34 acetic acid:0.6 hexanoic acid:0.8 stearic acid.
[5]Trivalent cation source was flash calcined alumina (FCA).

Solid CP-MAS $C^{13}$ NMR analyses of some of the hydrotalcites (Examples 1, 4, 6, 8, 12, 16, 17 and 18) indicated that in the majority of cases, the acids used in the preparations are indeed present in the carboxylate form. However, in a few instances (Examples 4, 6 and 8), a very small amount of the free acid is present with the corresponding anion, indicating an incomplete reaction in Step I.

Comparative Examples 25–29

Preparation of Commercially Prepared Hydrotalcite-Polypropylene Blends

Two approaches were taken to prepare blends of commercially prepared hydrotalcite with CHEMCOR® polypropylene emulsion:

1) the dried hydrotalcite was regelled in water, mixed with the emulsion, and then spray-dried, or 2) the emulsion was added to the hydrotalcite before it was spray-dried to obtain the blend.

Blends with HTC-0498-10 (LaRoche) from 5% to 81% by weight in the solid weight of polypropylene were prepared as indicated in Table III and analyzed by XRD, SEM, differential scanning calorimetry (DSC) and thermogravimetric analyses (TGA). Commercially prepared, HTC-0498-10 hydrotalcite had a limited regelling concentration of about 3% in warm water. This amount is much lower than the 8%–10% claimed by the manufacturer in its virgin gel before spray-drying. If this method of blend preparation were used, the low regelling concentration would require the use of large reactors.

TABLE III

BLENDS OF COMMERCIALLY PREPARED HYDROTALCITE AND POLYPROPYLENE[1]

| Comparative Example No. | Weight Percent Hydrotalcite | d spacing Å | DSC Maxima, °C. | TGA Percent Residue |
|---|---|---|---|---|
| 25 | 5 | 6.3 | 147, 380 | 9.6 |
| 26 | 9 | 6.2 | 147, 374 | 10.2 |
| 27 | 34 | 6.2 | 151, 329 | 22.4 |
| 28 | 38 | 6.2 | 151, 328 | 23.5 |
| 29 | 61 | 11.4 | 149, 331 | 46.1 |

[1]3% hydrotalcite HTC-0498-10 (LaRoche) was regelled in water at about 50° C. then polypropylene emulsion was added to the mixture.

The XRD analysis of the blends made from the commercially prepared hydrotalcite, HTC-0498-10, indicated a substantial decrease in d spacing from about 9.7 Å to 6.3 Å as the amount polypropylene became more than 60% as can be seen by reference to Table III, but increased when the level was about 19%. Without being limited to any specific theory, the Inventors believe that a reason for this drop may be due to possible exfoliation or dispersion of the synthetic hydrotalcite in the polymer matrix.

Figure 9:
FIG. 9 is a micrograph of a blend of about 5% hydrotalcite with polypropylene demonstrating a "doughnut" morphology.

FIG. 8, a SEM micrograph of Example 29, a blend containing about 81% hydrotalcite, showed a cabbage morphology that was better defined than that of the hydrotalcite from which it was obtained. The SEM, shown in FIG. 9, of a similar blend with 5% hydrotalcite from Example 25, however, had a what the Inventors herein term a "doughnut" morphology. Without being limited to any specific theory, the Inventors believe that the doughnut morphology may result from the hydrophilic portion of the synthetic hydrotalcite forming a circular core while the hydrophobic portion, which comprises stearate or octanoate anion mixed with the polymer matrix, surrounds the circular core. The radii of the doughnut particles ranged from 2–3 microns. The blend of Example 25 may have the hydrotalcite so highly dispersed in the polymer matrix that it no longer exists in a layered form.

Thermogravimetric analyses of blends made from the commercially prepared hydrotalcite, HTC-0498-10, and polypropylene yield residue percentages that are indicative of the amount of hydrotalcite in the material. The residue percentages increased with the hydrotalcite percentage in the preparation as can be seen in Table III and represent nonvolatile materials that remained after heating the sample to elevated temperatures.

The DSC transition temperatures represent the temperature at which phase changes take place in the blend and are indicative of minimum temperature required for processing these materials in polymer applications. The first phase transition temperature occurred at approximately 150° C. for the blends. Some of these materials exhibited lower transition temperatures that can be attributed to a, loss of water.

EXAMPLES 30–35

Preparation of Synthetic Hydrotalcite-Polyolefin Blends

Preparation method 1 described above for Comparative Examples 25–29 was also used to prepare blends from some of the synthetic hydrotalcites of the present invention, namely those from stearic acid, octanoic acid, vinylacetic acid, and a mixture of acetic, hexanoic, and stearic acids. These synthetic hydrotalcites did not exhibit the regelling problem associated with the commercially prepared hydrotalcite, HTC-0498-10, which became very difficult to stir when the hydrotalcite concentration was above 3%. The second approach of adding the polypropylene emulsion as a final step in the preparation of hydrotalcite before spray-drying was also tested with synthetic hydrotalcites prepared from methacrylic and acrylic acids.

An amount of the synthetic hydrotalcite, which will result in about 3% weight, was added to water. The temperature of this mixture was raised to about 40° to 60° C. and the required amount of polypropylene emulsion, depending on desired blend composition, was slowly added to the gel with vigorous stirring. Enough water was added to keep the mixture fluid. The mixture was heated to about 80° C. and maintained at that temperature for about one hour and cooled overnight to room temperature with continued stirring. The mixture was spray-dried at an inlet temperature of 230° C. and an outlet temperature of 90°–105° C. Each blend was subjected to XRD, SEM, TGA and DSC analyses. The results from Examples 30–35 are summarized in Table IV.

Synthetic hydrotalcite-polypropylene blends of stearic acid, octanoic acid, methyl methacrylic acid and acrylic acid were also prepared in a manner that required the addition of the polypropylene emulsion to the un-isolated synthetic hydrotalcite in the preparations. The resulting blend was isolated by spray-drying in the manner described above.

HTC-0498-10, as the first transition temperatures ranged from 148°–152° C. These materials can therefore be processed with polyolefins at normal temperatures.

Although the method of blending the hydrotalcites of the present invention with polyolefins is illustrated by the example of polypropylene, it will be readily apparent to those skilled in the art that other polyolefins can be used in the present invention such as polystyrene, polyvinylchloride, polyethylene, polybutylene and polymethyl pentane.

TABLE IV

SYNTHETIC HYDROTALCITE-POLYPROPYLENE BLENDS

| Example No. | Organic Anion Source | Percent Synthetic Hydrotalcite | Original d-spacing Å | d spacing Å | d spacing percent change | DSC Maxima, ° C. | TGA Percent Residue |
|---|---|---|---|---|---|---|---|
| 30 | Stearic acid[1] | 38 | 26.4 | 17.1 | −35.2 | 149 | 10.0 |
| 32 | Octanoic acid | 47 | 20.3 | 23.6 | +16.3 | 151 | 16.0 |
| 31 | Vinylacetic acid | 41 | 17.7 | 15.5 | −12.4 | 150 | 23.9 |
| 33 | Mixed acids[2] | 55 | 16.4 | 17.0 | +3.7 | 148 | 26.1 |
| 35 | Methacrylic acid[3] | 49 | 13.2 | 15.5 | +17.4 | 150 | 27.9 |
| 34 | Acrylic acid[3] | 57 | 16.6 | 13.7 | −17.5 | 152 | 37.2 |

[1]Stearic acid hydrotalcite made by method of example 2, i.e., in organic solvent.
[2]Mixed acids composed of the following molar ratio 1.34 acetic:0.6 hexanoic:0.8 stearic.
[3]Polypropylene emulsion was added to un-isolated synthetic hydrotalcite in the final mixture. All others were prepared by addition of previously isolated synthetic hydrotalcite that was regelled before polypropylene emulsion was added.

With the longer carbon chain synthetic hydrotalcites, the effect of the blend composition on the d spacings was mixed. As can be seen from a review of Table IV, with blends of synthetic hydrotalcites of stearic acid, vinylacetic acid and acrylic acid there were drops in the d spacing of 35.2%, 12.4%, and 17.5% respectively, even at hydrotalcite compositions ranging from 38%–57%. For octanoic acid, mixed acids (acetic, hexanoic and stearic), and methacrylic acid, the d spacing for the blends increased respectively by 16.3%, 3.7%, and 17.4% compared to the synthetic hydrotalcites from which they were derived. Without being limited to any specific theory, the inventors believe that these results may suggest a lack of uniform blending of the synthetic hydrotalcites with the polypropylene or that the structure of the organic anions have a different influence on the d spacing in the blend. The SEM micrographs of blends of polypropylene with synthetic hydrotalcites prepared from octanoic and from mixed acids (acetic, hexanoic and stearic acids) exhibited a doughnut morphology.

Figure 10:
FIG. 10 is a micrograph of a blend of methacrylic acid-derived hydrotalcite with polypropylene.
Figure 10:
Figure 10:
Figure 10:
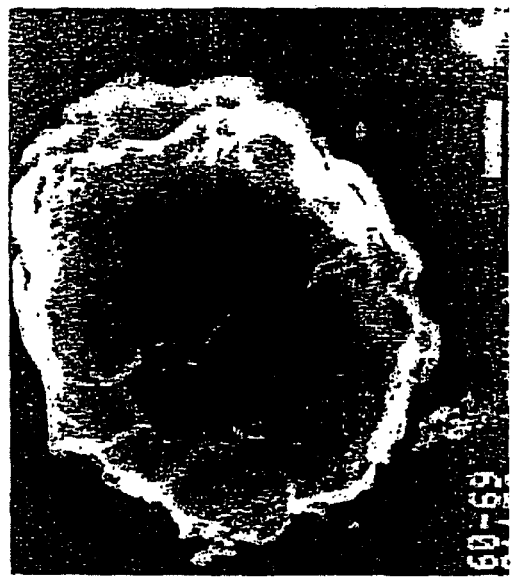
Figure 10:

FIG. 10, which is a SEM micrograph of Example 31, a methacrylic acid-derived synthetic hydrotalcite polypropylene blend, did not exhibit the doughnut morphology, nor was it what could be referred to as semi-cabbage. The particle size of the methacrylic acid-derived synthetic hydrotalcite-polypropylene blend averaged 5×3 angstroms.

As seen in Table IV, the residue percentages from TGA for the synthetic hydrotalcites made from anions other than acetate correlate with the hydrotalcite percentages in the blends when corrections are made for the contribution of the weight of the anion. The DSC transition temperatures for these materials were similar to those materials derived from

EXAMPLES 36–38

Methyl Methacrylate Polymerization in the Presence of Synthetic Methacrylic Acid-Derived Hydrotalcite The reactions were carried in a 1-liter CHEMCO® reactor under 20 psig nitrogen at a stirring rate of 400 rpm. The amounts of methyl methacrylate, methacrylic acid-derived hydrotalcite and the reaction temperatures were as shown in Table V. In each case, the reactor was charged with 460 ml water, 100 g methyl methacrylate and the desired amount of methacrylate acid-derived hydrotalcite. The reactor was first purged with nitrogen, then pressurized. 0.5 g AIBN (2,2-azobisisobutyronitrile) initiator and surfactant (Aerosol OT 75%, 2.5 g, available from Cytec Industries) were dissolved in 470 g methyl methacrylate and the solution was pumped (fed) at 88 ml/hr into the reactor which had been pre-heated to 70° C. The reaction continued until stirring became difficult due to the formation of solid product clumps. At that point, the methyl methacrylate feeding was stopped and the temperature was maintained for about 30 minutes to react any residual methyl methacrylate. After the reactor cooled to room temperature, polymer pieces were taken out and air-dried at room temperature, preferably in a fume hood. The amounts of polymer obtained are shown in Table V.

TABLE V

METHYL METHACRYLATE POYMERIZATION IN THE PRESENCE OF SYNTHETIC METHACRYLIC ACID DERIVED HYDROTALCITE

| Example No. | Methyl Methacrylate g | Methacrylic Acid-Derived Hydrotalcite g | Reaction temp. °C. | Reaction Time hours | Polymer Produced g | DSC °C., Maxima | TGA percent residue |
|---|---|---|---|---|---|---|---|
| 36 | 364 | 30 | 72–84 | 4 | 341 | 122, 258 | 3.9 |
| 37 | 306 | 10 | 75–90 | 4 | 256 | 115, 372 | 1.6 |
| 38 | 264 | 30 | 75–85 | 4 | 229 | 114, 374 | 7.5 |

Co-polymerizing the synthetic hydrotalcite derived from methacrylic acid with methyl methacrylate demonstrates that master-batch materials may be prepared. Blends with polyolefin, such as polypropylene, can then be prepared from these master batches. With the Aerosol OT surfactant, the copolymer was expected to be evenly slurried in the water in which the reaction was carried out. In all the examples, slurry formation occurred only at the beginning of the polymerization. As the polymer amount increased, the suspended particles coalesced into a ball or into chunks that forced the early termination of the polymerization because of difficulty with stirring. The product obtained was a tan, tough and stiff polymer.

TGA analyses of the products, as seen in Table V, indicated varying levels of the methyl methacrylic acid-derived hydrotalcite (1.6% to 8%) based on the residue percentage. This percentage is indicative of the amount of alumina and magnesium left after all the carbon sources in the samples have been volatilized. The examples with highest starting weight percent of hydrotalcite yielded the highest residue percentage. The first DSC transition temperatures (114°–122° C.) were only small diffuse peaks and may not be indicative of the real polymer transition temperature. The second transition at 370° C. was likely due to the phase changes in the copolymer, this may indicate the need for higher processing temperatures in polymer applications. These polymers dissolved or formed a clear gel in toluene, ethyl acetate, and, to a limited extent, in methylene chloride. The copolymer with the least amount of synthetic methacrylic acid-derived hydrotalcite (1.6% residue by TGA) was the most soluble in toluene. When the solution containing this copolymer was dried, a clear film with good adhesive characteristics was obtained.

The foregoing illustrations of embodiments of the present invention are offered for the purposes of illustration and not limitation. It will be readily apparent to those skilled in the art that the embodiments described herein may be modified or revised in various ways without departing from the spirit and scope of the invention. The scope of the invention is to be measured by the appended claims.

We claim:

1. A synthetic hydrotalcite of the general formula:

$$[M^{2+}_{1-x}M^{3+}_x(OH)_2]^{x+}[A^{n-}_{x/n}\cdot mH_2O]^{x-}$$

wherein $M^{2+}$ is a divalent cation, $M^{3+}$ is a trivalent cation and $A^{n-}$ is at least one organic anion comprising a vinylacetate,
said synthetic hydrotalicite being produced by reacting said trivalent cation, $M^{3+}$ with said at least one organic anion, $A^{n-}$ to produce an intermediate, and
reacting said intermediate with said divalent cation, $M^{2+}$ in water to produce said synthetic hydrotalcite.

2. The synthetic hydrotalcite of the general formula:

$$[M^{2+}_{1-x}M^{3+}_x(OH)_2]^{x+}[A^{n-}_{x/n}\cdot mH_2O]^{x-}$$

wherein $M^{2+}$ is a divalent cation, $M^{3+}$ is a trivalent cation and $A^{n-}$ is an anion comprising a mixture of at least two members selected from the group consisting of straight chain saturated carboxylates of $C_2$–$C_4$ acids, straight chain saturated carboxylates of $C_5$–$C_{18}$ acids, carboxylates of aromatic acids, unsaturated carboxylates of acrylic acid, unsaturated carboxylates of methacrylate acid and unsaturated carboxylates of vinylacetic acid,
said synthetic hydrotalicite being produced by reacting said trivalent cation, $M^{3+}$ with said anion, $A^{n-}$ to produce an intermediate, and
reacting said intermediate with said divalent cation, $M^{2+}$ in water to produce said synthetic hydrotalcite.

3. The synthetic hydrotalcite of claim 2, wherein said organic anion, $A^{n-}$ is a mixture of an acetate, a hexanoate and a stearate.

4. The synthetic hydrotalcite of claim 3, wherein the molar ratio of said mixture is about 1.34 acetate:0.6 hexanoate:0.8 stearate.

5. The synthetic hydrotalcite of claim 2, wherein said organic anion, $A^{n-}$ is a mixture of an acrylate, an acetate and a stearate.

6. The synthetic hydrotalcite of claim 5, wherein the molar ratio of said mixture is about 3.76 acrylate:1.14 acetate:0.57 stearate.

7. The synthetic hydrotalcite of claim 2, wherein said divalent cation, $M^{2+}$ comprises $Mg^{2+}$ and up to 50% of at least one divalent cation selected from the group consisting of: $Ni^{2+}$, $Co^{2+}$, $Zn^{2+}$, $Cu2+$ and $Mn^{2+}$.

8. The synthetic hydrotalcite of claim 2, wherein said trivalent cation, $M^{3+}$ comprises $Al^{3+}$ and up to 50% of at least one trivalent cation selected from the group consisting of: $Al^{3+}$, $Cr^{3+}$, and $Fe^{3+}$.

9. A synthetic hydrotalcite-polyolefin blend comprising:
a polyolefin; and
a synthetic hydrotalcite of the general formula:

$$[M^{2+}_{1-x}M^{3+}_x(OH)_2]^{x+}[A^{n-}_{x/n}\cdot mH_2O]^{x-}$$

wherein $M^{2+}$ is a divalent cation, $M^{3+}$ is a trivalent cation and $A^{n-}$ is an organic anion source comprising a mixture of at least two selected from the group consisting of: straight chain carboxylates of $C_5$–$C_{18}$ acids, carboxylates of aromatic acids, carboxylates of acrylic acid, unsaturated carboxylates of methacrylic acid and unsaturated carboxylates of vinylacetic acid,
said synthetic hydrotalcite being produced by reacting said trivalent cation, $M^{3+}$ with said anion, $A^{n-}$ to produce an intermediate, and reacting said intermediate with said divalent cation, $M^{2+}$ in water to produce said synthetic hydrotalcite.

10. The synthetic hydrotalcite-polyolefin blend of claim 9, wherein said organic anion, $A^{n-}$ is a mixture of an acetate, a hexanoate and a stearate.

11. The synthetic hydrotalcite-polyolefin blend of claim 9, wherein the molar ratio of said mixture is about 1.34 acetate:0.6 hexanoate:0.8 stearate.

12. The synthetic hydrotalcite-polyolefin blend of claim 9, wherein said organic anion, $A^{n-}$ is a mixture of an acrylate, an acetate and a stearate.

13. The synthetic hydrotalcite-polyolefin blend of claim 12, wherein the molar ratio of said mixture is about 3.76 acrylate:1.14 acetate:0.57 stearate.

14. The synthetic hydrotalcite-polyolefin blend of claim 9, wherein said polyolefin is polypropylene.

15. The synthetic hydrotalcite-polyolefin blend of claim 9, wherein said polyolefin is polyethylene.

16. The synthetic hydrotalcite-polyolefin blend of claim 9, wherein said polyolefin is polybutylene.

17. The synthetic hydrotalcite-polyolefin blend of claim 9, wherein said polyolefin is polymethyl pentane.

18. The synthetic hydrotalcite-polyolefin blend of claim 9, wherein said divalent cation, $M^{2+}$ contains $Mg^{2+}$ and up to 50% of at least one divalent cation selected from the group consisting of: $Ni^{2+}$, $Co^{2+}$, $Zn^{2+}$, $Cu^{2+}$ and $Mn^{2+}$.

19. The synthetic hydrotalcite-polyolefin blend of claim 9, wherein said trivalent cation, $M^{3+}$ contains $Al^{3+-}$ and up to 50% of at least one trivalent cation selected from the group consisting of: $Cr^{3+}$ and $Fe^{3+}$.

20. A synthetic hydrotalcite-polystyrene blend comprising:
a polystyrene; and
a synthetic hydrotalcite of the general formula:

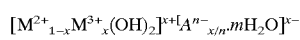

wherein $M^{2+}$ is a divalent cation, $M^{3+}$ is a trivalent cation and $A^{n-}$ is an organic anion source comprising a mixture of at least two members selected from the group consisting of: straight chain carboxylates of $C_5$–$C_{18}$ acids, carboxylates of aromatic acids, carboxylates of acrylic acid, unsaturated carboxylates of methacrylic acid and unsaturated carboxylates of vinylacetic acid, said synthetic hydrotalcite being produced by reacting said trivalent cation, $M^{3+}$ with said anion, $A^{n-}$ to produce an intermediate, and reacting said intermediate with said divalent cation, $M^{2+}$ in water to produce said synthetic hydrotalcite.

21. The synthetic hydrotalcite-polystyrene blend of claim 20, wherein said divalent cation, $M^{2+}$ consists essentially of $Mg^{2+}$.

22. The synthetic hydrotalcite-polystyrene blend of claim 20, wherein said trivalent cation, $M^{3+}$ consists essentially of $Al^{3+}$.

23. The synthetic hydrotalcite-polystyrene blend of claim 20, wherein said organic anion, $A^{n-}$ is selected from the group consisting of hexanoates, octanoates, decanoates, stearates, benzoates, chlorobenzoates, naphthoates, p-hydroxybenzoates, acrylates, methacrylates and vinylacetates.

24. The synthetic hydrotalcite-polystyrene blend of claim 20, wherein said organic anion, $A^{n-}$ is a mixture of an acetate, a hexanoate and a stearate.

25. The synthetic hydrotalcite-polystyrene blend of claim 20, wherein the molar ratio of said mixture is about 1.34 acetate: 0.6 hexanoate 0.8 stearate.

26. The synthetic hydrotalcite-polystyrene blend of claim 20, wherein said organic anion, $A^{n-}$ is a mixture of an acrylate, an acetate and a stearate.

27. The synthetic hydrotalcite-polystyrene blend of claim 26, wherein the molar ratio of said mixture is about 3.76 acrylate: 1.14 acetate: 0.57 stearate.

28. The synthetic hydrotalcite-polystyrene blend of claim 20, wherein said divalent cation, $M^{2+}$ contains $Mg^{2+}$ and up to 50% of at least one divalent cation selected from the group consisting of: $Ni^{2+}$, $Co^{2+}$, $Zn^{2+}$, $Cu^{2+}$ and $Mn^{2+}$.

29. The synthetic hydrotalcite-polystyrene blend of claim 20, wherein said trivalent cation, $M^{3+}$ contains $Al^{3+}$ and up to 50% of at least one trivalent cation selected from the group consisting of: $Cr^{3+}$ and $Fe^{3+}$.

30. A synthetic hydrotalcite-polyvinylchloride blend comprising:
a polyvinylchloride; and
a synthetic hydrotalcite of the general formula:

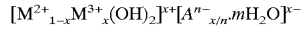

wherein $M^{2+}$ is a divalent cation, $M^{3+}$ is a trivalent cation and $A^{n-}$ is an organic anion source comprising a mixture of at least two members selected from the group consisting of: straight chain carboxylates of $C_5$–$C_{18}$ acids, carboxylates of aromatic acids, carboxylates of acrylic acid, unsaturated carboxylates of methacrylic acid and unsaturated carboxylates of vinylacetic acid, said synthetic hydrotalcite being produced by reacting said trivalent cation, $M^{3+}$ with said anion, $A^{n-}$ to produce an intermediate, and reacting said intermediate with said divalent cation, $M^{2+}$ in water to produce said synthetic hydrotalcite.

31. The synthetic hydrotalcite-polyvinylchloride blend of claim 30, wherein said divalent cation, $M^{2+}$ consists essentially of $Mg^{2+}$.

32. The synthetic hydrotalcite-polyvinylchloride blend of claim 30, wherein said trivalent cation, $M^{3+}$ consists essentially of $Al^{3+}$.

33. The synthetic hydrotalcite-polyvinylchloride blend of claim 30, wherein said organic anion, $A^{n-}$ is selected from the group consisting of hexanoates, octanoates, decanoates, stearates, benzoates, chlorobenzoates, naphthoates, p-hydroxybenzoates, acrylates, methacrylates and vinylacetates.

34. The synthetic hydrotalcite-polyvinylchloride blend of claim 30, wherein said organic anion, $A^{n-}$ is a mixture of an acetate, a hexanoate and a stearate.

35. The synthetic hydrotalcite-polyvinylchloride blend of claim 30, wherein the molar ratio of said mixture is about 1.34 acetate: 0.6 hexanoate: 0.8 stearate.

36. The synthetic hydrotalcite-polyvinylchloride blend of claim 30, wherein said organic anion, $A^{n-}$ is a mixture of an acrylate, an acetate and a stearate.

37. The synthetic hydrotalcite-polyvinylchloride blend of claim 36, wherein the molar ratio of said mixture is about 3.76 acrylate: 1.14 acetate: 0.57 stearate.

38. The synthetic hydrotalcite-polyvinylchloride blend of claim 30, wherein said divalent cation, $M^{2+}$ contains $Mg^{2+}$ and up to 50% of at least one divalent cation selected from the group consisting of: $Ni^{2+}$, $Co^{2+}$, $Zn^{2+}$, $Cu^{2+}$ and $Mn^{2+}$.

39. The synthetic hydrotalcite-polyvinylchloride blend of claim 30, wherein said trivalent cation, $M^{3+}$ contains $Al^{3+-}$ and up to 50% of at least one trivalent cation selected from the group consisting of: $Cr^{3+}$ and $Fe^{3+}$.

* * * * *